(12) United States Patent
Vogt (10) Patent No.: US 10,549,042 B2
(45) Date of Patent: *Feb. 4, 2020

(54) BOTULINUM TOXIN PREFILLED GLASS SYRINGE

(71) Applicant: MERZ PHARMA GMBH & CO. KGAA, Frankfurt am Main (DE)

(72) Inventor: Markus Vogt, Frankfurt am Main (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/536,503

(22) PCT Filed: Dec. 22, 2015

(86) PCT No.: PCT/EP2015/002602
§ 371 (c)(1),
(2) Date: Jun. 15, 2017

(87) PCT Pub. No.: WO2016/102068
PCT Pub. Date: Jun. 30, 2016

(65) Prior Publication Data
US 2017/0340823 A1    Nov. 30, 2017

(30) Foreign Application Priority Data

Dec. 23, 2014  (EP) .................... 14004394

(51) Int. Cl.
| | |
|---|---|
| *A61M 5/31* | (2006.01) |
| *A61K 38/48* | (2006.01) |
| *A61Q 19/08* | (2006.01) |
| *A61K 9/00* | (2006.01) |
| *A61M 5/315* | (2006.01) |
| *A61K 47/26* | (2006.01) |
| *A61K 47/42* | (2017.01) |

(52) U.S. Cl.
CPC ......... *A61M 5/3129* (2013.01); *A61K 9/0019* (2013.01); *A61K 38/4893* (2013.01); *A61K 47/26* (2013.01); *A61K 47/42* (2013.01); *A61M 5/31513* (2013.01); *A61Q 19/08* (2013.01); *C12Y 304/24069* (2013.01); *A61M 2005/3131* (2013.01); *A61M 2205/0222* (2013.01); *A61M 2205/0238* (2013.01)

(58) Field of Classification Search
None
See application file for complete search history.

(56) References Cited

U.S. PATENT DOCUMENTS

| | | | | |
|---|---|---|---|---|
| 8,383,103 B2* | 2/2013 | Gaylis | ................. | A61K 9/0019 424/236.1 |
| 8,535,062 B2* | 9/2013 | Nguyen | ................. | G09B 23/30 434/267 |
| 9,554,968 B2* | 1/2017 | Weikart | ................. | A61J 1/00 |
| 9,662,450 B2* | 5/2017 | Jones | ................. | A61M 5/31513 |
| 9,827,282 B2* | 11/2017 | Naheed | ................. | A61K 36/185 |
| 9,863,042 B2* | 1/2018 | Jones | ................. | C23C 16/401 |
| 9,937,099 B2* | 4/2018 | Weikart | ................. | C23C 16/045 |
| 10,010,362 B2* | 7/2018 | Vogt | ................. | A61B 17/8833 |
| 10,406,290 B2* | 9/2019 | Vogt | ................. | A61K 9/0019 |
| 2006/0269575 A1 | 11/2006 | Hunt | | |
| 2007/0134199 A1 | 6/2007 | Frevert | | |
| 2008/0045889 A1 | 2/2008 | Gerondale | | |
| 2009/0010965 A1 | 1/2009 | Eisele et al. | | |
| 2009/0028906 A1 | 1/2009 | Grein et al. | | |
| 2013/0078295 A1* | 3/2013 | Cebrian Puche | ........ | A61K 8/64 424/401 |
| 2013/0211344 A1 | 8/2013 | Rodriguez et al. | | |
| 2014/0249484 A1 | 9/2014 | Jones et al. | | |
| 2015/0290080 A1* | 10/2015 | Weikart | ................. | C23C 16/045 206/438 |
| 2015/0297800 A1* | 10/2015 | Weikart | ................. | A61M 5/3129 600/432 |
| 2016/0175408 A1* | 6/2016 | Chang | ................. | A61K 38/063 604/506 |
| 2016/0184413 A1* | 6/2016 | Taylor | ................. | A61K 8/345 424/94.67 |
| 2016/0199464 A1* | 7/2016 | Barnett | ................. | A61K 38/51 424/94.5 |
| 2016/0346480 A1* | 12/2016 | Gleason | ............. | A61K 38/4893 |
| 2017/0100306 A1* | 4/2017 | Weikart | ................. | A61J 1/00 |

(Continued)

FOREIGN PATENT DOCUMENTS

| | | |
|---|---|---|
| CN | 101687046 A | 3/2010 |
| CN | 103930595 A | 7/2014 |

(Continued)

OTHER PUBLICATIONS

Wortznnan et al, Aesthet. Surg. J., Nov./Dec. 2009, 29/6S:S34-S42 (Year: 2009).*
International Search Report Dated of PCT/EP2015/002602 dated Mar. 15, 2016.
European Medicines Agency. "NeuroBloc: EPAR: Scientific Discussion," (2008), 1-18.
Health Network, NTUH. "Botox Beauty," Special Question Newspaper Guide, (2006), 1-4.
Third Party Observation for application No. EP20150823134, dated Jul. 10, 2019.
Wohlfarth, et al., "Pharmacokinetic Properties of Different Formulations of Botulinum Neurotoxin Type A," Movement Disorders, (2004), vol. 19, Suppl. 8, pp. S65-S67.

(Continued)

*Primary Examiner* — Nita M. Minnifield
(74) *Attorney, Agent, or Firm* — McBee Moore & Vanik IP, LLC (57) ABSTRACT

The present invention relates to a prefilled glass container, such as a prefilled glass syringe, comprising an aqueous *botulinum* toxin formulation. The aqueous *botulinum* toxin formulation in the prefilled container is stable at low to ambient temperature for a prolonged time period. Furthermore, the present invention relates to a kit comprising the *botulinum* toxin prefilled container, and to the use of the *botulinum* toxin prefilled container in therapeutic and cosmetic applications.

16 Claims, 3 Drawing Sheets

(56) References Cited

U.S. PATENT DOCUMENTS

| | | | |
|---|---|---|---|
| 2017/0134199 A1 | 5/2017 | Wang et al. | |
| 2017/0173267 A1 * | 6/2017 | Ashmead | A61M 5/31513 |
| 2017/0232198 A1 * | 8/2017 | Jones | A61M 5/31513 604/230 |
| 2017/0340823 A1 * | 11/2017 | Vogt | A61K 38/4893 |
| 2018/0015225 A1 * | 1/2018 | Vogt | A61K 38/4893 |
| 2019/0201630 A1 * | 7/2019 | Vogt | A61K 38/4893 |

FOREIGN PATENT DOCUMENTS

| | | | | |
|---|---|---|---|---|
| EP | 1997509 A1 * | 12/2008 | | A61K 9/0019 |
| EP | 2048156 A1 * | 4/2009 | | A61K 38/4893 |
| EP | 2311512 A2 | 4/2011 | | |
| EP | 3236939 A1 * | 11/2017 | | A61K 38/4893 |
| EP | 3253364 A1 * | 12/2017 | | A61K 38/4893 |
| JP | 2003-522154 A | 7/2003 | | |
| JP | 2012-531442 | 12/2012 | | |
| JP | 2014-533177 A | 12/2014 | | |
| KR | 100 753 765 B1 | 8/2007 | | |
| WO | 00/15245 A2 | 3/2000 | | |
| WO | 01/58472 A2 | 8/2001 | | |
| WO | 2006005910 A2 | 1/2006 | | |
| WO | 2006008595 A1 | 1/2006 | | |
| WO | 2008145358 A1 | 12/2008 | | |
| WO | 2008145359 A1 | 12/2008 | | |
| WO | 2009003010 A2 | 12/2008 | | |
| WO | WO-2008145359 A1 * | 12/2008 | | A61K 9/0019 |
| WO | 2009008595 A1 | 1/2009 | | |
| WO | 2010096134 A1 | 8/2010 | | |
| WO | 2010/151840 A2 | 12/2010 | | |
| WO | 2012047950 A1 | 4/2012 | | |
| WO | 2013071138 A1 | 5/2013 | | |
| WO | 2014/014641 A1 | 1/2014 | | |
| WO | 2014/026161 A1 | 2/2014 | | |
| WO | WO-2014026161 A1 * | 2/2014 | | A61K 31/714 |
| WO | 2014052792 A1 | 4/2014 | | |
| WO | 2016/066821 A1 | 5/2016 | | |
| WO | WO-2016102068 A1 * | 6/2016 | | A61K 38/4893 |
| WO | WO-2016124213 A1 * | 8/2016 | | A61K 38/4893 |
| WO | WO-2016187087 A1 * | 11/2016 | | F01L 1/185 |
| WO | WO-2017220553 A1 * | 12/2017 | | A61M 5/178 |

OTHER PUBLICATIONS

Third Party Observation for application No. EP20150823134, dated Aug. 7, 2019.

* cited by examiner

BOTULINUM TOXIN PREFILLED GLASS SYRINGE

CROSS REFERENCE TO RELATED APPLICATIONS

This application is a § 371 National Stage Application of PCT/EP2015/002602, filed 22 Dec. 2015, which claims priority to EP 14004394.4 filed 23 Dec. 2014.

FIELD OF THE INVENTION

The present invention relates to a prefilled glass container, such as a prefilled glass syringe, comprising an aqueous *botulinum* toxin formulation. The aqueous *botulinum* toxin formulation in the prefilled container is stable at low to ambient temperature for a prolonged time period. Furthermore, the present invention relates to a kit comprising the *botulinum* toxin prefilled container, and to the use of the *botulinum* toxin prefilled container in therapeutic and cosmetic applications.

BACKGROUND OF THE INVENTION

The stability of pharmaceutical products is of paramount importance to ensure safe and efficacious use for a sufficiently long time period. Unfortunately, the performance (safety, reliability, and efficacy) of most pharmaceutical products deteriorates over time. The causes of drug deterioration include chemical degradation (e.g., hydrolysis, oxidation, reduction and racemization), microbial contamination, and other mechanisms (e.g., precipitation).

Proteinaceous active ingredients are often of a labile nature and inherently instable. This leads to loss of biological activity during production, reconstitution and/or storage of protein-containing pharmaceutical compositions. These problems observed with proteins may be due to chemical instability, resulting in bond formation or cleavage (e.g., hydrolysis, oxidation, racemization, β-elimination and disulfide exchange), and/or due to physical instability of the second or higher-order structure of proteins without covalent bond-breaking modification (e.g., denaturation, adsorption to surfaces, and non-covalent self-aggregation).

Since degradation reactions are generally fastest in aqueous solutions and slowest in solid dosage forms, protein active ingredients are often formulated as lyophilized (i.e. freeze-dried) products. However, the lyophilized products have generally to be reconstituted with a pharmaceutically acceptable liquid (e.g., saline) prior to use. Therefore, lyophilized pharmaceutical products are considered less convenient than other dosage forms. Further, lyophilized products are usually more expensive and time-consuming to manufacture. Moreover, mismanagement can occur during the reconstitution process resulting in inaccurate dosing or sterility issues. All these disadvantageous can be overcome by the use of prefilled syringes. Therefore, prefilled syringes have been become increasingly popular as drug delivery devices.

However, if proteins are used as active ingredients, the limited stability of proteins rendered it often impossible for formulation scientists to use a prefilled syringe format. This applies especially to very dilute aqueous solutions of *botulinum* toxin (*botulinum* neurotoxin, BoNT). Such BoNT solutions are used in the treatment of a wide range of debilitating neuromuscular diseases (e.g., cervical dystonia, blepharospasm, spasticity, and hyperhidrosis) and in aesthetic medicine (e.g., treatment of facial wrinkles). There are seven homologous serotypes (A-G) of *botulinum* toxin, which are produced by different *Clostridium* spp., in particular *C. botulinum*, in the form of a complex consisting of a neurotoxic polypeptide and other (non-toxic) clostridial proteins (i.e. different hemagglutinins and a nontoxic, non-hemagglutinating protein). The neurotoxic polypeptide has a molecular weight of about 150 kDa and is activated by selective proteolytic cleavage to yield the active two-chain form consisting of a heavy chain (HC; includes the translocation domain and receptor-binding domain) and a light chain (LC; includes the catalytic domain) linked by a disulfide bond and non-covalent interactions.

*Botulinum* toxins are inherently instable and, in particular, are known to be highly unstable at alkaline pH and heat-labile. Additionally, it is known that dilution of the isolated toxin complex from milligram quantities to the much lower toxin concentrations used in solutions for injection (in the nanograms per milliliter range) presents significant difficulties because of the rapid loss of specific activity upon such great dilution.

Therefore, commercial preparations of *botulinum* toxin often come as vacuum-dried or lyophilized material. Examples include, for example, Botox® (onabotulinumtoxinA; Allergan, Inc.) and Dysport® (abobotulinumtoxinA; Ipsen Ltd.), which both contain the *C. botulinum* toxin complex of type A. Another example is Xeomin® (incobotulinumtoxin; Merz Pharma GmbH & Co. KGaA), which contains the pure neurotoxic component of serotype A (i.e. the neurotoxic polypeptide of a molecular weight of about 150 kDa) and is devoid of any other proteins of the *Clostridium botulinum* toxin complex (i.e. the different hemagglutinins and the nontoxic, non-hemagglutinating protein).

However, the lyophilized toxin products have a number of drawbacks including the need for reconstitution prior to use and concomitant sterility issues. In addition, the reconstituted toxin solution is often not entirely used in the clinical practice because not every patient and indication requires the same dosage. The unused amount of the reconstituted toxin solution can be stored at lower temperatures, but only for a short period of time. For example, after dilution with normal saline prior to use, Botox® and Dysport® are recommended to be used within 6 hours and 4 hours, respectively. Likewise, the package leaflet of Xeomin® specifies that after storage for more than 24 hours, the reconstituted Xeomin® solution shall no longer be used than for 24 hours and is then to be discarded.

To increase toxin stability, stabilizing proteins such as human serum albumin (HSA) are often added in the art. Other stabilizing strategies involve the use of non-proteinaceous stabilizing agents, for example surfactants, polyvinylpyrrolidone (PVP), disaccharides, polyols and the like. In addition, it was disclosed in WO 00/15245 that a liquid formulation of highly concentrated *botulinum* toxin type B (about 2500 U/ml) is stable for up to 30 months when stored in glass vials at 5° C. However, this prolonged stability requires buffering the pH of the formulation down to an acidic pH of between 5 and 6, which causes pain upon injection. Other known approaches to increase toxin stability rely on the addition of various non-protein excipients which, however, are unsuitable or undesirable for human use (see, e.g., WO 01/58472, WO 2006/005910, and WO 2007/041664).

Thus, there is still no injectable *botulinum* toxin presentation available which is not only stable over a long period to provide a sufficiently long shelf life, but is also convenient and easy to use, reduces medication errors, and minimizes the risk of contamination.

OBJECTIVE OF THE INVENTION

In view of the above, the objective of the present invention is to provide a medical dosage form for the administration of *botulinum* toxin, which has a long shelf life and is convenient, safe and easy to use.

SUMMARY OF THE INVENTION

The above object is solved by the provision of a *botulinum* toxin prefilled container (e.g., a syringe, vial, carpule, or ampoule) which is characterized by a superior long-term stability of the liquid *botulinum* toxin formulation in the container.

In a first aspect, the present invention provides a prefilled glass container (e.g., a syringe, vial, carpule, or ampoule) comprising an aqueous *botulinum* toxin formulation, wherein the toxin activity is not reduced by more than 25%, preferably by not more than 20%, relative to the initial toxin activity, upon storage of the prefilled container (e.g., a syringe, vial, carpule, or ampoule) for (a) 12 months at 5° C., (b) 12 months at 25° C., or (c) 6 months at 30° C.

The stability of the aqueous *botulinum* toxin formulation in the prefilled container (e.g., a syringe, vial, carpule, or ampoule) in terms of the count of subvisible particles equal to or greater than 10 µm is also excellent and generally below 1000/ml during storage for 6 to 24 months (e.g., 6, 9, 12, 15, 18 or 24 months) at 2-30° C. (e.g., at 5° C., 25° C. or 30° C.). Furthermore, the aqueous *botulinum* toxin formulation exhibits an excellent pH stability as indicated by a pH value that is generally not increased or decreased by more than 10%, relative to the initial pH value, during storage of the prefilled container (e.g., a syringe, vial, carpule, or ampoule) for 6 to 24 months (e.g., 6, 9, 12, 15, 18 or 24 months) at 2-30° C. (e.g., at 5° C., 25° C. or 30° C.).

In another aspect, the present invention provides a kit comprising a prefilled glass container (e.g., a syringe, vial, carpule, or ampoule) according to the first aspect of the invention and, optionally, instructions for use of said prefilled glass container.

In a further aspect, the present invention provides a prefilled glass container (e.g., a syringe, vial, carpule, or ampoule) according to the first aspect of the present invention for use in therapy. For example, the prefilled glass container (e.g., a syringe, vial, carpule, or ampoule) may be used for treating a disease or condition caused by or associated with hyperactive cholinergic innervation of muscles or exocrine glands in a patient including, but not limited to, dystonia, spasticity, paratonia, diskinesia, focal spasm, strabismus, tremor, tics, migraine, sialorrhea and hyperhidrosis.

In still another aspect, the present invention relates to the use of the prefilled glass container (e.g., a syringe, vial, carpule, or ampoule) according to the first aspect of the invention for use in cosmetic treatments, such as for treating wrinkles of the skin and facial asymmetries, e.g. glabellar frown line, crow's feet, upper facial rhytides and platysma bands.

In a yet further aspect, the present invention provides a method for treating a disease or condition caused by or associated with hyperactive cholinergic innervation of muscles or exocrine glands in a patient, the method comprising locally administering an effective amount of *botulinum* toxin to a muscle or exocrine gland of the patient using the prefilled container (e.g., a syringe, vial, carpule, or ampoule) according to the first aspect of the invention.

In a still further aspect, the present invention relates to a method for the cosmetic treatment of the skin, such as for treating wrinkles of the skin and facial asymmetries, the method comprising locally administering an effective amount of *botulinum* toxin to a patient by intradermal, subdermal or subcutaneous injection using the prefilled glass container (e.g., a syringe, vial, carpule, or ampoule) according to the first aspect of the present invention.

Further embodiments of the present invention are set forth in the appended dependent claims. The present invention may be more fully understood by reference to the following detailed description of the invention, the examples and the accompanying drawings.

DETAILED DESCRIPTION OF THE INVENTION

The present invention is based on the surprising finding that a liquid *botulinum* toxin formulation in a glass container (e.g., in the form of a syringe, vial, carpule or ampoule) is stable after storage for a prolonged period of time at reduced temperature (e.g., 2-8° C.) and even at ambient temperature (e.g., 20-30° C., in particular 25° C.). The *botulinum* toxin prefilled container of the present invention therefore advantageously exhibits an extended shelf life.

Moreover, the high long-term stability provides tolerance against interruptions of the cool chain and may facilitate the approval procedure and/or the commercialization in all climate zones, including countries with hot climate. Furthermore, the prefilled glass container of the present invention, in particular the syringe format, presents several additional advantages in comparison to other administration forms, such as easy and convenient use, reduced risk of medication errors, high dosing accuracy, low risk of contamination, improved sterility assurance, and/or high safety in administration.

As used herein, a "prefilled container" refers to any device having a partially or fully enclosed space that can be sealed or is sealed and can be used to contain, store, and/or transport liquid formulations. A "prefilled container" within the meaning of the present invention is preferably a closed (or sealed) container made of, or partially or predominantly made of, glass and includes, for example, containers in the form of (i) a syringe, (ii) a vial, (iii) a carpule, or (iv) an ampoule.

Prefilled syringes and carpules have two openings that are sealed to prevent leakage of the contents (e.g., aqueous formulations). In case of a prefilled syringe, the proximal end is sealed by a plunger stopper and the distal end is sealed by a capping device, as explained in detail herein below. In case of a glass carpule, which is generally a glass cylinder sterile filled with a drug formulation, the proximal end is typically sealed by a rubber stopper. This rubber stopper can be pressed in as a piston in the cylinder by the pressure of a punch of the carpule syringe. The distal end is typically sealed by a puncture membrane. The puncture membrane is pierced for injection.

A "vial" within the meaning of the present invention is a vessel, which has usually a tubular form or a bottle-like shape with a neck and is suitable for containing, storing, and/or transporting drug formulations. The single opening is sealable by different vial closure systems. For example, vials may be closed with a screw cap (screw vials), a stopper of cork, plastic or rubber (lip vials and crimp vials) and other closure systems like flip-tops or snap caps. Within the present invention a "vial" preferably means a glass vessel having its opening sealed with a vial closure system.

In the following, the present invention is described in more detail. It is pointed out that, although the term "prefilled syringe", "prefilled glass syringe", "syringe" or "glass syringe" is used in the detailed description of the invention, this does not mean that it is limited to a (glass) syringe as a particular embodiment of the (glass) container. In fact, any reference herein to a "prefilled syringe", "prefilled glass syringe", "syringe", "glass syringe" or the like is to be understood as a reference to, and disclosure of, a "container" or "glass container" and also includes, or discloses, a "vial" or "glass vial", a "carpule" or "glass carpule", or an "ampoule" or "glass ampoule", unless otherwise stated.

In a first aspect, the present invention relates to a prefilled glass syringe comprising *botulinum* toxin in an aqueous formulation, wherein the toxin activity is not reduced by more than 25%, relative to the initial toxin activity, upon storage of the prefilled syringe for (a) 12 months at standard refrigerator temperatures (i.e. 2-8° C., such as 5° C.), (b) 12 months at 25° C., or (c) 6 months at 30° C. Preferably, the toxin activity is not reduced by more than 20% or 15%, relative to the initial toxin activity, upon storage of the prefilled syringe for (a) 12 months at 2-8° C. (e.g., 5° C.), (b) 12 months at 25° C., or (c) 6 months at 30° C. More preferably, the toxin activity is not reduced by more than 20% or 15%, relative to the initial toxin activity, upon storage of the prefilled syringe for (a) 6 months at 2-8° C. (e.g., 5° C.), (b) 6 months at 25° C., or (c) 3 months at 30° C. Particularly preferable, the toxin activity is not reduced by more than 10%, relative to the initial toxin activity, upon storage of the prefilled syringe for (a) 3 to 6 months at 2-8° C. (e.g., 5° C.) or (b) 3 to 6 months at 25° C. Especially preferable, the toxin activity is not reduced by more than 5%, relative to the initial toxin activity, upon storage of the prefilled syringe for (a) 3 to 6 months at 2-8° C. (e.g., 5° C.) or (b) 3 to 6 months at 25° C.

Surprisingly, the aqueous *botulinum* toxin formulation in the prefilled syringe is also stable for even longer storage times of up to 24 months or even longer. For example, upon storage for up to 24 months (e.g., 15, 18 or 24 months) at 2-8° C. (e.g., 5° C.) or 25° C., the toxin activity is preferably not reduced by more than 30% or 25%, more preferably by no more than 20%, in particular by no more than 15%, particularly preferable by no more than 10%, and most preferable by no more than 5%, relative to the initial toxin activity.

In particular, the toxin activity is preferably not reduced by more than 25%, 20%, 15%, 10% or 5%, relative to the initial toxin activity, upon storage of the prefilled syringe for 24 months at 2-8°. Upon storage of the prefilled syringe at 2-8° for 18 months, the toxin activity is preferably not reduced by more than 25%, 20%, 15%, 10% or 5%, relative to the initial toxin activity. Furthermore, the toxin activity is preferably not reduced by more than 35%, 30%, 25%, 20% or 15%, relative to the initial toxin activity, upon storage of the prefilled syringe for 24 months at 25° C. Upon storage of the prefilled syringe at 25° C. for 18 months, the toxin activity is preferably not reduced by more than 30%, 25%, 20%, 15% or 10%, relative to the initial toxin activity.

Within the present invention, the term "toxin activity" is intended to refer to the biological activity of the *botulinum* toxin. "Biological activity" may refer to (a) receptor binding, (b) internalization, (c) translocation across the endosomal membrane into the cytosol, and/or (d) endoproteolytic cleavage of proteins involved in synaptic vesicle membrane fusion. For example, any LC (ligh chain) domain, which shows proteolytic activity of more than 10%, 20%, 30%, 40%, 50%, 60%, 70%, 80%, 90% and up to 100% of the corresponding wild-type LC domain in a SNAP-25 assay may be considered "biological active" or "to exhibit proteolytic activity" within the scope of this invention. Furthermore, any HC (heavy chain) domain that is capable of binding to a cellular HC domain receptor, in particular to its native HC domain receptor, and is capable of translocating an LC domain attached to it, is considered "biologically active".

The biological activity is expressed in Mouse Units (MU). As used herein, 1 MU is the amount of neurotoxic component, which kills 50% of a specified mouse population after intraperitoneal injection, i.e. the mouse i.p. $LD_{50}$, as measured in accordance with the method of Schantz and Kauter (Schantz and Kauter, J. Assoc. Off. Anal. Chem. 1978, 61:96-99). The terms "MU" and "Unit" or "U" are used interchangeably herein.

Suitable assays for assessing the biological activity include the mouse hemidiaphragm assay (MHA) described by Pearce et al. (Toxicol. Appl. Pharmacol. 128:69-77, 1994), the hemidiaphragm assay (HDA) according to Goschel et al. (Experimental Neurology 147:96-102, 1997), the mouse diaphragm assay (MDA) according to Dressler et al. (Mov. Disord. 20:1617-1619, 2005), the SNAP-25 protease assay (e.g., the "GFP-SNAP25 fluorescence release assay" described in WO 2006/020748 or the "improved SNAP25 endopeptidase immuno-assay" described in Jones et al., 2008, J. Immunol. Methods 329:92-101), the electrochemoluminescence (ECL) sandwich ELISA described in WO 2009/114748, and cell-based assays as those described in WO 2009/114748, WO 2004/029576, WO 2013/049508 and, in particular, WO 2014/207109.

As used herein, the term "initial toxin activity" or "initial potency" generally refers to the activity of the *botulinum* toxin at the beginning of the storage period, i.e. after manufacture of the final, sterilized *botulinum* toxin prefilled syringe, in particular directly after manufacture or within one or two days after manufacture. Further, the term "upon storage", as used herein is intended to mean after storage for a certain time period. In addition, the term "during storage" generally means over the course of the entire storage period.

Furthermore, the aqueous *botulinum* toxin formulation is highly stable in terms of the subvisible particle count. A "subvisible particle" within the meaning of the present invention is typically a particle with a diameter below 100 μm. Specifically, the count (or number) of particles equal to or greater than 10 µm in the aqueous *botulinum* toxin formulation is typically below 1000/ml, preferably below 600/ml and more preferably below 200/ml during storage for 6 to 24 months (e.g., 6, 9, 12, 15, 18 or 24 months) at 2-30° C. (e.g., at 5° C., 25° C. or 30° C.).

Particle measurements may be conducted by different methods, such as Micro-Flow Imaging (MFI), Resonant Mass Measurement (RMM), and Nanoparticle Tracking Analysis (NTA). The particle measurements usually follow USP <788>. Within the context of the present invention, the Micro-Flow Imaging measurement is preferably used. This measurement method may, for example, be conducted using a DPA-5200 particle analyzer system (ProteinSimple, Santa Clara, Calif., USA) equipped with a silane coated high-resolution 100 µm flow cell. Generally, the samples are analyzed undiluted.

Alternatively, Resonant Mass Measurements (RMM) may be employed to determine the number of particles using, for example, the ARCHIMEDES Particle Metrology System (Affinity Biosensors, Santa Barbara, Calif., USA) equipped with a microsensor (size range 0.3-4 µm) calibrated with 1 µm polystyrene standards. All samples are typically analyzed without dilution. The results may be analyzed using the *ParticleLab* software (v1.8.570) with a size bin step of 10 nm. As another alternative for determining the particle count, Nanoparticle Tracking Analysis (NTA) may be used, for example, using a NanoSight LM20 system (NanoSight, Amesbury, UK). The samples are typically measured undiluted. Movements of the particles in the samples may be recorded as videos for 60 seconds at ambient temperature and analyzed using suitable software (e.g., the NTA 2.3 Software).

Moreover, the aqueous *botulinum* toxin formulation shows high pH stability in that the pH value is essentially stable during storage of the prefilled syringe. Preferably, the pH value is not increased or decreased by more than 10%, 8% or 6%, relative to the initial pH value, upon storage of the prefilled syringe for 6 to 24 months (e.g., 6, 9, 12, 15, 18 or 24 months) at 2-30° C. (e.g., at 5° C., 25° C. or 30° C.), for example for 18 months at 25° C. or for 24 months at 25° C. The pH may be measured in accordance with the US Pharmacopeia standardized test method USP <791>, which outlines pH measurements for a multitude of pharmaceutical product. Any suitable pH meter may be used, for example the Lab 870 pH meter of Schott Instruments.

As used herein, the term "prefilled syringe" refers to a syringe which is filled with a drug composition (i.e. the aqueous *botulinum* toxin formulation) prior to distribution to the end user who will administer the drug to the patient. A prefilled syringe typically includes a drug containment container forming part of a syringe body (i.e. a syringe barrel), a plunger to seal the proximal opening of the syringe and for expelling the drug, and a sealing device (e.g., a tip cap or a needle shield) on the outlet end of the syringe (e.g., the open end of the syringe tip or of a pre-mounted needle (cannula)) to seal the distal outlet opening. The term "prefilled glass syringe", as used herein, refers to a prefilled syringe, of which at least the barrel is made of glass.

Within the present invention, the prefilled syringe is preferably a Luer slip or Luer lock syringe equipped with a tip cap (if no needle is pre-mounted) or a needle shield (if the needle is pre-mounted). Within the meaning of the present invention, a "luer slip syringe" is a syringe that allows a needle to be pushed on to the end of the tip, whereas a "Luer-Lock syringe" is a syringe that allows a needle to be twisted onto the tip and then locked in place. This provides a secure connection and prevents accidental removal of the needles of the injection of fluids.

The prefilled syringe according to the present invention is generally sterilized and, thus, ready-to-use. Further, the prefilled syringe described herein is usually intended for single use and intended to be disposable. Prior to sterilization, the syringe, more specifically the inner surface of the glass syringe barrel, is typically coated with a lubricant to ease gliding of the plunger stopper and extruding of the syringe content. Suitable methods for sterilization include, but are not limited to, gamma radiation, ethylene oxide (ETO) treatment and moist heat (e.g., autoclaving).

In accordance with the present invention, the aqueous *botulinum* toxin formulation in the prefilled syringe contains the *botulinum* toxin at a concentration of, for example, 1 U/ml to 3000 U/ml, 10 U/ml to 1000 U/ml. Preferably, the *botulinum* toxin is present at a concentration of about 10 U/ml to 400 U/ml, more preferably about 25 U/ml to 200 U/ml, and most preferably about 40 U/ml to 150 U/ml (e.g., 50 U/ml, 75 U/ml or 100 U/ml).

The term "*botulinum* toxin", as used herein, broadly refers to any form and type of *botulinum* toxin. In particular, the *botulinum* toxin may be selected from *botulinum* toxin types A, B, C1, D, E, F, G, or mixtures thereof. Within the context of the present invention, the *botulinum* toxin is preferably of serotype A, B or C1, in particular serotype A.

Furthermore, the term "*botulinum* toxin", as used herein, is intended to include both the *botulinum* toxin complex (the "toxin complex") and the "neurotoxic component" of a *botulinum* toxin complex. As used herein, the term "*botulinum* toxin complex*" or "toxin complex" refers to a high molecular weight complex comprising the neurotoxic component of approximately 150 kDa and, in addition, non-toxic proteins of *Clostridium botulinum*, including hemagglutinin and non-hemagglutinin proteins. The *botulinum* toxin serotype A complex is commercially available, for example, as Botox® (Allergan, Inc.) or as Dysport® (Ipsen, Ltd.).

The term "neurotoxic component", as used herein, relates to the neurotoxic polypeptide of the toxin complex (the "150 kDa" polypeptide) without any associated non-toxic proteins. The pure neurotoxic component is, for example, commercially available under the trade names Xeomin® and Bocouture® (Merz Pharmaceuticals GmbH). Within the present invention, the *botulinum* toxin is preferably the neurotoxic component of a *botulinum* toxin complex of, e.g., serotype A, B, C1, in particular of a *botulinum* toxin complex of serotype A. In other words, the aqueous *botulinum* toxin formulation contained in the prefilled glass syringe preferably contains (only) said neurotoxic component and is devoid of any other protein of the *Clostridium botulinum* toxin complex.

It is also contemplated that the present invention encompasses isoforms, homologs, orthologs and paralogs of *botulinum* toxin that show at least 50%, at least 60%, at least 70%, at least 80%, at least 90% and up to 60%, up to 70%, up to 80%, up to 90%, up to 100% sequence identity to wild-type *botulinum* toxin, e.g. wild-type *botulinum* toxin A or the neurotoxic component of *botulinum* toxin of serotype A1 deposited with the GenBank database under the accession number AAA23262. The sequence identity can be calculated by any algorithm suitable to yield reliable results, for example by using the FASTA algorithm (W. R. Pearson & D. J. Lipman PNAS (1988) 85:2444-2448). Sequence identity may be calculated by comparing two polypeptides or two domains such as two LC domains or fragments thereof.

Modified and recombinant *botulinum* toxins are also within the scope of the present invention. With respect to suitable mutants, reference is made to WO 2006/027207, WO 2009/015840, WO 2006/114308, WO 2007/104567, WO 2010/022979, WO 2011/000929 and WO 2013/068476, which are all incorporated by reference herein. Furthermore, the present invention also refers to *botulinum* toxins, which are chemically modified, e.g. by pegylation, glycosylation, sulfatation, phosphorylation or any other modification, in particular of one or more surface or solvent exposed amino acid(s). The modified, recombinant, isoforms, homologs, orthologs, paralogs and mutants suitable for use in the present invention are biologically active, i.e. able to translocate into neurons and cleave proteins of the SNARE complex (e.g., VAMP/syntaxin, synaptobrevin, and SNAP-25) to exert its acetylcholine inhibitory effects, e.g., its muscle paralyzing effects.

Within the context of the present invention, the aqueous *botulinum* toxin formulation may comprise various other pharmaceutically acceptable substances, for example, salts (e.g., sodium chloride), stabilizing proteins (e.g., albumin, gelatin), sugars (e.g., glucose, fructose, galactose, trehalose, sucrose and maltose), carbohydrate polymers (e.g., hyaluronic acid and polyvinylpyrollidone (PVP)), polyols (e.g. glycerol and sugar alcohols like mannitol, inositol, lactitol, isomalt, xylitol, erythritol, sorbitol), amino acids, vitamins (e.g. vitamin C), zinc, magnesium, anesthetic agents (e.g., local anesthetic agents like lidocaine), surfactants, tonicity modifiers, and the like. The term "pharmaceutically acceptable", as used herein, refers to those compounds or substances which are suitable for contact with the tissues of mammals, especially humans.

The term "comprise", as used herein, is intended to encompass both the open-ended term "include" and the closed term "consist (of)". The term "made of", as used herein, is intended to broadly relate to "produced of/from", in particular mainly produced from, and generally means "comprising" (indicating that other substances or materials may be included in some amounts). It may also mean "consisting of".

Preferably, the pH of the aqueous *botulinum* toxin formulation in the prefilled syringe is between 6.0 to 7.5, 6.5 to 7.5, 6.1 to 7.3, 6.2 to 7.2, 6.3 to 7.1, and 6.5 to 7.0 during storage. A pH within the range of 6.1 to 7.3 is advantageous in that injections of such neutral or only slightly acidic solutions are much less painful upon injection than acidic solutions.

The term "aqueous formulation" or "aqueous *botulinum* toxin formulation", as used herein, is not particularly limited and may refer to an aqueous suspension, aqueous dispersion, aqueous emulsion and is preferably an aqueous solution.

Preferably, the aqueous *botulinum* toxin formulation does not contain a buffer substance like a phosphate buffer, a phosphate-citrate buffer, a lactate buffer, an acetate buffer and the like. The term "buffer" as used herein denotes a pharmaceutically acceptable excipient, which stabilizes the pH of a pharmaceutical preparation. Furthermore, the aqueous *botulinum* toxin formulation may be free of amino acids (e.g., methionine) and/or surfactants (e.g., polysorbates such as polysorbate 80) and/or animal-derived proteins (e.g., human serum albumin (HSA) or bovine serum albumin (BSA)).

A preferred aqueous *botulinum* toxin formulation for use herein comprises water, *botulinum* toxin (e.g., the neurotoxic component of *botulinum* toxin, preferably of type A) at a concentration such as 10 to 150 U/ml, a salt (e.g., sodium chloride) in a concentration such as 0.5% to 1.5% w/v, a sugar (e.g., a mono- or disaccharide, such as glucose, fructose, galactose, trehalose, sucrose and maltose) at a concentration such as 0.1% to 2% w/v, and a stabilizing protein (e.g., albumin) at a concentration such as 0.01% to 4% w/v, 0.1% to 3% w/v, or 0.1% to 1% w/v.

Another preferred aqueous *botulinum* formulation for use herein essentially consists of water, *botulinum* toxin (e.g. the neurotoxic component of *botulinum* toxin type A), sodium chloride, sucrose, and albumin (e.g., human serum albumin; HSA). The concentration of the mentioned components may be in the following ranges: 10 to 200 U/ml or 30 to 125 U/ml (*botulinum* toxin), 0.5% to 1.5% w/v or 0.7% to 1.1% w/v (sodium chloride), 0.1% to 2% w/v or 0.2% to 1% w/v (sucrose), 0.01% to 1% w/v, 0.05% to 0.5% w/v, 0.1% to 3% w/v or 0.5% to 1.5% w/v (HSA). A further preferred *botulinum* toxin formulation for use herein is a Xeomin® solution, e.g., reconstituted with physiological saline (0.9% sodium chloride), including 20 to 150 U/ml of the neurotoxic component of *botulinum* toxin type A.

The term "essentially consists of", as used herein is intended to mean that substances other than those indicated are only contained in trace amounts, e.g. unavoidable impurities contained in the components used for formulating the aqueous *botulinum* toxin formulation, and low amounts of impurities included in the isolated *botulinum* toxin (e.g., the neurotoxic component of *botulinum* toxin type A) as a result of the purification procedure (e.g., very low residual amounts of buffers, chelating agents and the like).

In accordance with the present invention, the configuration of the prefilled syringe is not particularly limited and commonly comprises a fluid-receiving barrel that, after filling, is removably capped by a capping device to sealingly close the distal end of the syringe (e.g., by a "cap" (or "tip cap") that is removed and replaced by a needle prior to use, or a sealing means like a needle shield in case of a syringe with a removable or permanent needle), and is closed at the proximal end by its plunger or any other means that is in fluid-tight engagement with the inner wall of the barrel. To use the prefilled syringe, the tip cap, needle shield or other type of capping device are removed, optionally a needle is attached (if not already present), and the plunger tip or piston is advanced in the barrel to inject the contents of the barrel into a patient.

The prefilled glass syringe according to the present invention preferably comprises:
(a) a syringe barrel made of glass including a proximal end and a distal end, and a generally cylindrical wall extending therebetween and defining a barrel lumen, the syringe barrel having a distally projecting tip with a fluid passage extending therethrough and communicating with the barrel lumen, wherein the generally cylindrical wall has an interior surface optionally coated with a barrier layer,
(b) a capping device having an outlet engaging portion sealingly engaging and closing the distal open outlet end of the syringe, wherein the outlet engaging portion is made of an elastomeric material that optionally has a coating on its surface, and
(c) a plunger rod assembly which extends into the proximal end of the syringe barrel and includes a plunger stopper in sliding fluid-tight engagement with the cylindrical wall of the barrel lumen, wherein the plunger stopper is made of an elastomeric material, which optionally has a coating on at least a portion of the plunger stopper that contacts the aqueous *botulinum* toxin formulation during storage and/or injection.

Generally, primary container closure systems, including components such as syringe barrels, sealing devices (e.g., tip caps or needle shields) and plungers, have the potential to interact with the drug formulation in the prefilled syringe. This may lead to the release of extractables/leachables from the syringe materials that contact the aqueous *botulinum* toxin formulation. The extractables/leachables have the potential to contaminate the aqueous *botulinum* toxin formulation and to impair the stability or activity of the *botulinum* toxin. Therefore, the materials of the prefilled syringe are generally selected to minimize or limit the amount of extractables and leachables.

As used herein, the terms "extractable(s)" and "leachable(s)" refer to chemical species that can be released from a container or component of material of the prefilled syringe and/or has migrated from syringe materials into the aqueous *botulinum* toxin formulation under normal conditions of use or storage. Methods for identification of extractables/leachables are known in the art and based on recommended industry practices and International Conference for Harmonisation (ICH) guidelines (see FDA guidance, Container Closure Systems for Packaging Human Drugs and Biologics), and include, e.g., Liquid Chromatography/Mass Spectrophotometry (LC/MS), Gas Chromatography Spectroscopy/Mass Spectrophotometry (GC/MS), Inductively Coupled Plasma (ICP) and Infrared (IR).

The inside surface of the glass barrel is usually coated with a lubricant layer (herein also referred to, and interchangeably used with, the term "barrier layer" or "barrier coating"). The lubricant layer should not only provide high lubricity, enabling the plunger to easily glide through the barrel, but also be compatible with the aqueous *botulinum* toxin formulation and protect its shelf life. Within the context of the present invention, the lubricant layer may be a silicone-free lubricant layer or a silicone lubricant layer.

Likewise, the inner surface of the glass vessel part of the vial, the inner surface of the glass cylinder of the carpule, and the inner surface of the glass ampoule may be optionally coated with a barrier layer and, in particular, with a silicone-free layer or a silicone layer. Thus, all comments provided below with regard to the silicone-free lubricant layer and the silicone lubricant layer of the glass syringe equally apply to the silicone-free layer and silicone layer, respectively, of the glass vial, glass carpule and glass ampoule.

A suitable silicone-free lubrication layer is, for example, a fluoropolymer layer (e.g., fluoropolymer (fluorocarbon) layers, such as ethylene-tetrafluoroethylene (ETFE) layers and perfluoropolyether-based (PFPE-based) layers (e.g., TriboGlide®)), as well as silicon oxide-based glass PECVD (plasma-enhanced chemical vapor deposition) coatings.

The silicone-free lubrication layer can be prepared as known in the art, for example by spraying glass syringe barrels with a perfluoropolyether oil to achieve a thin layer of lubricant on the inside surface of the syringe, followed by exposing the inner cavities to a downstream inert gas (e.g., argon or helium) plasma. The plasma treatment leads to crosslinking of the perfluoropolyether, thereby immobilizing the coating and reducing its tendency to migrate off the target surface, resulting in less particles that potentially impairs the stability/efficacy of the *botulinum* toxin drug. An exemplary production process is described in WO 2014/014641 A1, the content of which is incorporated herein by reference. Furthermore, a particularly suitable silicone-free barrier coating for use herein is known in the art as TriboGlide® coating, a perfluoropolyether coating crosslinked by plasma treatment.

A suitable silicone lubricant layer for use herein may be prepared by a siliconization method selected from, but not limited to, silicone oil-based methods (e.g., spray-on siliconization or baked-on siliconization) and vapor deposition methods (e.g., plasma enhanced chemical vapor deposition (PECVD)). Preferably, the silicone lubricant layer is formed by spray-on siliconization or, more preferably, by baked-on siliconization.

In the spray-on siliconization method, a silicone oil (e.g. DOW CORNING® 360 with a viscosity of 1000 cSt) is sprayed into the syringe (i.e. the barrel) using, e.g., a diving or static nozzle to produce a thin silicone oil layer. While silicone oil is an excellent lubricant, excess silicone oil can lead to the formation of unwanted visual and subvisual silicone oil particles. With protein-based drugs, in particular, these silicone oil particles may lead to undesirable interactions with protein drugs. For example, subvisual silicone oil particles are thought to promote protein aggregation. Therefore, since it results in fewer sub-visual and visual silicone oil particles, the baked-on siliconization processes is particularly preferred for use herein. It involves the application of silicone oil as an emulsion (e.g., DOW CORNING® 365 siliconization emulsion), which is then baked on the glass surface at a specific temperature and for a specific time.

The design of the syringe barrel is not particularly limited and typically has an inside diameter adjusted to accommodate the desired fill volume of, e.g., 0.5 cm$^3$, 1.0 cm$^3$, 1.5 cm$^3$ or 2.0 cm$^3$. Usually, the syringe barrel has graduated marks indicating the volume of fluid in the syringe. In addition, the syringe barrel may include a flange-style interface. The design of the flange may, for example, be compatible with ISO11040. The flange-style interface may further be compatible with an optionally present handle. Furthermore, in case of a Luer-Lock syringe, the syringe may be equipped with a Luer-Lock adaptor of, e.g., polycarbonate.

The syringe tip is usually integrally formed with the syringe barrel. The tip is formed with an integral passage extending axially through the tip and being in communication with the chamber for dispensing the contents of the syringe barrel. The tip may have a substantially frustoconical shape that converges from the distal outlet end of the syringe barrel towards the tip's outlet end. Alternatively, the tip may be characterized as divergent (i.e., expanding from a smaller diameter to a larger one). Furthermore, the tip is usually located centrally in relation to the body of the syringe (concentric syringe tip) but may also be located offset towards the edge of the body (eccentric syringe tip).

The "capping device" within the meaning of the present invention broadly refers to any means for closing and sealing the open outlet end of a syringe. Within the present invention, the term "open outlet end" refers to any distal open end of a syringe that is in fluid communication with the barrel lumen. The capping device generally has a channel with a closed end and an open end having a dimension for receiving and efficiently sealing the open outlet end of the syringe to prevent leakage.

In case of prefilled syringes without pre-mounted needles, the capping device is a capping means commonly known as "tip cap". The tip cap forms a fluid-tight seal with the tip of the syringe to efficiently close the syringe barrel and to prevent leakage of the contents of the syringe barrel. The tip cap is usually removable coupled to the syringe tip or a luer collar. The luer collar surrounds the top of the syringe barrel (e.g., syringe tip). Preferably, the luer collar has internal threads and the tip cap has external threads complementing said internal threads of said luer collar for coupling the tip cap to the syringe barrel. The luer collar is typically a separately molded luer collar that is mounted directly to the tip of the syringe barrel, e.g., by a snap or interference fit. Prior to use, the tip can be removed, and a needle cannula (or needle/needle assembly) can then be securely coupled to the syringe tip.

If the prefilled syringe includes a removable or non-removable (permanent) cannula (also referred to as "needle" or "needle assembly") extending from the syringe tip for delivering the aqueous *botulinum* toxin formulation from said syringe, the capping device may be referred to as "needle shield". Said needle shield generally has a channel with a closed end and an open end having a dimension for receiving and coupling with the cannula (needle) mounted on the tip of the syringe. Typically, the (sharpened) end of the cannula penetrates the closed end of the channel in the needle shield to seal the open end of the cannula.

The capping device (e.g., tip cap or needle shield) may be a unitary member and is usually made from a flexible and/or resilient polymeric material (e.g., an elastomer), at least a portion of which contacts and seals the distal opening of the syringe (referred to as the "outlet engaging portion"). Alternatively, the capping device may have an outer cap made of a rigid plastic material that is coupled to a flexible and/or resilient inner cap made of a flexible and resilient polymeric material (e.g., an elastomer), wherein at least a portion of the inner cap contacts and seals the distal opening of the syringe (referred to as the "outlet engaging portion").

In view of the fact that the outlet engaging portion contacts the aqueous *botulinum* toxin formulation during storage and/or use, it is preferably made of a material having a minimized potential for unwanted extractables/leachables. To this end, the outlet engaging portion may have a coating thereon to increase compatibility with the aqueous *botulinum* toxin formulation.

Suitable flexible and/or resilient materials of the capping device, in particular of the outlet engaging portion, include elastomers that do not interfere with the aqueous *botulinum* toxin formulation and enable long-term storage. In particular, the part of the sealing device that contacts the aqueous *botulinum* toxin formulation, i.e. the outlet engaging portion, should exhibit low extractable/leachable levels during prolonged storage of the aqueous *botulinum* toxin formulation. As used herein, the term "elastomeric" or "elastomeric material" refers primarily to crosslinked thermosetting rubbery polymers that are more easily deformable than plastics but that are approved for use with pharmaceutical grade fluids and are not readily susceptible to leaching or gas migration.

Preferably, the elastomeric material is selected from isoprene rubber (IS), butadiene rubber (polybutadiene, BR), butyl rubber (copolymer of isobutylene and isoprene; IIR), halogenated butyl rubber (e.g., chloro butyl rubber, CIIR; and bromo butyl rubber: BIIR), styrene-butadiene rubber (copolymer of styrene and butadiene, SBR), and mixtures thereof. Preferably, the elastomeric material is a styrene-butadiene rubber, a butyl rubber, a blend of isoprene rubber and a halogenated (e.g. bromo or chloro) butyl rubber, a halogenated butyl rubber, particularly a bromo butyl rubber or a chloro butyl rubber, or a mixture thereof. The elastomeric material may also be reinforced with an inert mineral. Further, it may be cured (e.g., with organic peroxide, phenolic resins, etc.).

Suitable coatings that may be optionally present on the elastomeric material are made of a material that does not undesirably interfere with the aqueous *botulinum* toxin formulation and exhibits low levels of extractables/leachables. A preferred example of such a coating is a coating made of a fluoropolymer, i.e. a fluorocarbon coating. Other suitable coatings for use herein include, for example, polypropylene, polyethylene, parylene (e.g., parylene N, parylene C and parylene HT), and crosslinked silicone (e.g., the B2-coating (Daikyo Seiko) or XSi™ (Becton Dickinson)).

The fluoropolymer coatings include, but are not limited to, fluorinated ethylene-propylene copolymers (e.g., tetrafluoroethylene-hexafluoropropylene copolymer (FEP)), fluorinated ethylene-ethylene copolymers (e.g., ethylene tetrafluoroethylene copolymer (ETFE), such as FluroTec®), PVA (a copolymer of tetrafluoroethylene (TFE) and perfluoropropylvinylether (PPVE)), tetrafluoroethylene-perfluoroethylene copolymers, polyvinylidene fluoride (PVDF), polyvinyl fluoride (PVF), polytetrafluoroethylene (PTFE), and mixtures thereof. Preferably, the coating is made of ETFE and, particulary, is a FluroTec® coating.

With regard to the carpule of the present invention, the distal end is sealed by a puncture membrane. The puncture membrane may be formed from a thin rubber or silicone, a thin plastic/polymer, a film such as Mylar, a polyolefin such as polyethylene or polypropylene, a metal foil such an aluminum foil, etc. The membrane may be between about 0.001 and 2.0 mm, usually between 0.002 mm and 0.65 mm thick. Also, the membrane may be made of an elastomeric material and optionally have a coating as described above in connection with the capping device of the prefilled glass syringe.

With regard to the vial of the present invention, the vial closure system (e.g., cap), in particular those portions of the vial closure system that come into contact with, or have the potential to come into contact with and/or seal the vial (e.g., a septum) may be made of an elastomeric material, in particular a thermoplastic elastomeric material, more particularly a styrenic block copolymer thermoplastic elastomer, or of an elastomeric material as described above in connection with the capping device of the prefilled glass syringe of the present invention. Another suitable material is a silicone material. Furthermore, the said materials may have an optional coating, in particular a fluoropolymer coating, as defined above in relation to the capping device of the prefilled glass syringe.

In accordance with the present invention, the prefilled syringe commonly includes a plunger rod assembly, which extends into the proximal end of the syringe barrel. The plunger rod assembly may include a rod (also known as pushrod) with a plunger stopper at its tip (also known as "plunger") in sliding fluid-tight engagement with the cylindrical wall of the barrel lumen. The plunger forms the proximal seal and the dynamic seal that allows for extrusion of the liquid *botulinum* toxin formulation. The plunger stopper contacts the aqueous *botulinum* toxin formulation during storage and/or administration. Therefore, the plunger stopper should be compatible with the aqueous *botulinum* toxin formulation and not impair its long-term stability. In particular, the plunger stopper should preferably be designed to minimize the amount of extractables/leachables upon long-time storage.

Within the present invention, the plunger stopper is preferably made of an elastomeric material, which optionally has a coating on at least a portion of the plunger stopper that contacts the aqueous *botulinum* toxin formulation during storage and/or use. Suitable plunger stopper elastomeric materials for use herein include, but are not limited to, isoprene rubber (IS), butadiene rubber (polybutadiene, BR), butyl rubber (copolymer of isobutylene and isoprene, IIR), halogenated butyl rubber (e.g., chloro butyl rubber, CIIR; and bromo butyl rubber, BIIR), styrene-butadiene rubber (copolymer of styrene and butadiene, SBR), and mixtures thereof. Preferably, the plunger stopper material is a butyl rubber or a halogenated butyl rubber or a mixture thereof, more preferably a bromo butyl rubber or a chloro butyl rubber, and most preferably a butyl rubber. The elastomeric material may also be reinforced with an inert mineral. Further, it may be cured (e.g., with organic peroxide, phenolic resins, etc.).

Preferably, the plunger stopper comprises a coating acting as a barrier film. The coating is usually applied to at least the seal surfaces, including the surface portion of the plunger stopper facing the barrel lumen and contacting the aqueous *botulinum* toxin formulation during storage and/or use. The coating serves the purpose of minimizing interaction between the plunger and the liquid *botulinum* toxin formulation and to provide good lubricity.

Suitable coatings of the plunger stopper are generally made of a material that does not undesirably interfere with the aqueous *botulinum* toxin formulation and exhibits low levels of extractables/leachables. Such coatings include, but are not limited to, polypropylene, polyethylene, parylene (e.g., parylene N, parylene C and parylene HT), crosslinked silicone and, preferably, fluoropolymer coatings. Examples of suitable crosslinked silicone coatings include the B2-coating (Daikyo Seiko) or XSi™ (Becton Dickinson).

The fluoropolymer coatings include, but are not limited to, fluorinated ethylene-propylene copolymers (e.g., tetrafluoroethylene-hexafluoropropylene copolymer (FEP)), fluorinated ethylene-ethylene copolymers (e.g., ethylene tetrafluoroethylene copolymer (ETFE), such as FluroTec®), PVA (a copolymer of tetrafluoroethylene (TFE) and perfluoropropylvinylether (PPVE)), tetrafluoroethylene-perfluoroethylene copolymers, polyvinylidene fluoride (PVDF), polyvinyl fluoride (PVF), polytetrafluoroethylene (PTFE), and mixtures thereof. Preferably, the coating is made of ETFE and, particulary, is a FluroTec® coating.

The design of the plunger stopper is not particularly limited and may be a nested or bagged stopper. Further, the interface to the rod may be threaded to allow installation of the rod after sterilization. Alternatively, the interface to the rod may be designed with a snap-on design. The rod, like the plunger stopper, is generally designed to withstand sterilization but is not otherwise limited in any particular way. Typically, the rod is made of a plastic material such as an ethylene vinyl acetate (EVA) copolymer or a polypropylene.

The rubber stopper of the carpule of the present invention may be made of the same elastomeric materials as described above in connection with the plunger stopper of the glass syringe. Also, the rubber stopper of the carpule may have the same optional coating as defined above with respect to the coating on the plunger stopper. Further, the coating may be on at least a portion of the rubber stopper that contacts the aqueous *botulinum* toxin formulation during storage and/or use.

The prefilled syringe of the present invention meets the industry standard with regard to extractables, such as defined by the foaming test, pH test, potassium permanganate-reducing substances test, UV spectrum test and residue on evaporation test according to The Japanese Pharmacopoeia, No. 61, *Test Methods for Plastic Containers* (2001). Furthermore, the prefilled syringe and the respective component before and after sterilization satisfy the standards of The Japanese Pharmacopoeia, 14th Edition, No. 59, *Test for Rubber Closure for Aqueous Infusions*.

In another aspect, the present invention relates to a kit comprising a prefilled glass container (e.g., a syringe, vial, carpule or ampoule) according to the present invention and, optionally, instructions for use of said prefilled glass container.

In a further aspect, the present invention relates to a prefilled glass syringe according to the present invention for use in therapy. In particular, the prefilled glass container (e.g., a syringe, vial, carpule or ampoule) according to the present invention may be used in the treatment of a disease or condition caused by or associated with hyperactive cholinergic innervation of muscles or exocrine glands in a patient.

Within the context of the present invention, if the container is not a syringe (e.g., a vial, carpule or ampoule), the content of these "non-syringe type" containers (i.e. the aqueous *botulinum* toxin formulation) is generally injected to the desired target site using a suitable injection device (e.g., a syringe) in the same manner as described herein in relation to the prefilled glass syringe. The carpules are inserted into a carpule injection device as known to those skilled in the art. The contents of the vials and ampoules are generally aseptically filled into a syringe and then injected to the target site using a suitable injection device (e.g., a syringe) in the same manner as described herein in relation to the prefilled glass syringe.

The term "hyperactive cholinergic innervation", as used herein, relates to a synapse, which is characterized by an unusually high amount of acetylcholine release into the synaptic cleft. "Unusually high" relates to an increase of, e.g., up to 25%, up to 50% or more with respect to a reference activity which may be obtained, for example, by comparing the release with the release at a synapse of the same type but which is not in a hyperactive state, wherein muscle dystonia may be indicative of the hyperactive state. "Up to 25%" means, for example, about 1% to about 25%. Methods for performing the required measurements are known in the art.

Within the present invention, the disease or condition caused by or associated with hyperactive cholinergic innervation of muscles includes, but is not limited to, dystonias (e.g., blepharospasm, spasmodic torticollis, limb dystonia, and task-specifc dystonias such as writer's cramps), spasticities (e.g., post-stroke spasticity, spasticity caused by cerebral palsy), paratonia, diskinesias (e.g., tardive diskinesia) focal spasms (e.g., hemifacial spasm), (juvenile) cerebral palsy (e.g., spastic, dyskinetic or ataxic cerebral palsy), strabismus, pain (e.g. neuropathic pain), wound healing, tremors, tics, and migraine.

The prefilled *botulinum* toxin container (e.g., a syringe, vial, carpule or ampoule) of the present invention is particularly useful in the treatment of dystonia of a muscle. Exemplary dystonias include, but are not limited to, dystonias selected from the group consisting of (1) cranial dystonia, including blepharospasm and oromandibular dystonia of the jaw opening or jaw closing type, (2) cervical dystonia, including antecollis, retrocollis, laterocollis and torticollis, (3) pharyngeal dystonia, (4) laryngeal dystonia, including spasmodic dysphonia, (5) limb dystonia, including arm dystonia such as task specific dystonias (e.g., writer's cramp), leg dystonia, axial dystonia, segmental dystonia, and (6) other dystonias.

The "hyperactive exocrine gland" to be treated within the context of the present invention is not particularly limited and covers any exocrine gland with hyperactivity. It is therefore envisaged that the present invention can be applied to the treatment involving any of the glands mentioned in Sobotta, Johannes, Atlas der Anatomie des Menschen. 22. Auflage. Band 1 and 2, Urban & Fischer, 2005, which is incorporated herein by reference. Preferably, the hyperactive gland is an autonomic exocrine gland. The *botulinum* toxin composition is preferably injected into or in the vicinity of the hyperactive exocrine gland.

Within the present invention, the hyperactive exocrine gland may be selected from the group consisting of sweat gland, tear gland, salivary gland and mucosal gland. Alternatively, the hyperactive gland may also be may be associated with a disease or condition selected from the group consisting of Frey syndrome, Crocodile Tears syndrome, axillar hyperhidrosis, palmar hyperhidrosis, plantar hyperhidrosis, hyperhidrosis of the head and neck, hyperhidrosis of the body, rhinorrhea, or relative hypersalivation in patients with stroke, Parkinson's disease or amyotrophic lateral sclerosis. In particular, the disease or condition caused by or associated with hyperactive cholinergic innervation of exocrine glands may include drooling (hypersalivation, sialorrhea) and excessive sweating (hyperhidrosis).

The administration is not limited to any particular administration regimen, mode, form, dose and interval. As known to those skilled in the art, the administered amount or dose of *botulinum* toxin depends on the mode of application, the type of disease, the patient's weight, age, sex and state of health, and which target tissues are chosen for injection. The *botulinum* toxin formulation is usually administered locally, e.g., by subcutaneous or intramuscular injection into or in the vicinity of the target tissues (e.g., muscles, skin, exocrine glands).

Furthermore, different muscles, depending on their size, generally require different dosing. A suitable dose may range from 10 to 2000 U, preferably from 50 to 500 U, and more preferably from 100 to 350 U of *botulinum* toxin. For the treatment of exocrine glands, the dose is usually in the range of 10 to 500 U, preferably 20 to 200 U, and more preferably 30 to 100 U. Such total amounts may be administered on the same day or on a subsequent day of treatment. For example, during a first treatment session a first fraction of the dose may be administered. During one or more treatment sessions, the remaining fraction of the total dose may be administered. Further, the frequency of application is not particularly limited and suitable administration intervals may be three months or less (e.g., 4 or 8 weeks) or more than three months.

In still another aspect, the present invention relates to the use of the prefilled glass container (e.g., a syringe, vial, carpule or ampoule) of the present invention for cosmetic applications, such as for treating facial asymmetries and wrinkles and lines of the skin (e.g., facial lines and facial wrinkles), such as upper facial rhytides, platysma bands, glabellar frown lines, nasolabial folds, chin folds, marionette lines, buccal commissures, perioral wrinkles, crow's feet, and jawlines. Preferably, the prefilled *botulinum* toxin container (e.g., a syringe, vial, carpule or ampoule) of the present invention is used for injection into glabellar frown lines, horizontal forehead lines, crow's feet, perioral folds, mental ceases, popply chin, and/or platysmal bands.

The amounts of *botulinum* toxin administered for cosmetic application are usually in the range of 1 to 5 U, 5 to 10 U, 10 to 20 U or 20 to 50 U. Such total amounts may be administered on the same day or on a subsequent day of treatment. For example, during a first treatment session a first fraction of the dose may be administered. This first fraction is preferably a suboptimal fraction, i.e. a fraction, which does not remove the wrinkles or skin lines completely. During one or more treatment sessions, the remaining fraction of the total dose may be administered.

In a yet further aspect, the present invention relates to a method of treating a disease or condition caused by or associated with hyperactive cholinergic innervation of muscles or exocrine glands in a patient, the method comprising locally administering an effective amount of *botulinum* toxin to a muscle or exocrine gland of the patient using the prefilled glass container (e.g., a syringe, vial, carpule or ampoule) according to the first aspect of the invention.

The term "effective amount", as used herein, refers to the amount of a *botulinum* toxin sufficient to effect beneficial or desired therapeutic, cosmetic or anesthetic result. In the present context, the term "local administration" within the meaning of the present invention refers preferably to subcutaneous or intramuscular injection into or in the vicinity of the target tissues (e.g., muscles, skin, exocrine glands). The term "patient", as used herein, generally relates to a human afflicted with a disease or condition caused by or associated with hyperactive cholinergic innervation of muscles or exocrine glands in a patient, or to a human in need of a cosmetic or anesthetic treatment. As used herein, "patient" may be interchangeably used with "subject" or "individual".

The administration is not limited to any particular administration regimen, mode, form, dose and interval. As used herein, the term "to the muscle or exocrine gland" means that the *botulinum* toxin may be administered into, or in vicinity of, one or more muscles or exocrine glands. Usually, the *botulinum* toxin is administered by local intramuscular injection. With respect to further details regarding the administration (e.g., regimen, mode, form, dose and interval) and the disease or conditions to be treated, the same comments apply as those set out above in relation to the use of the prefilled glass container (e.g. prefilled *botulinum* toxin syringe) for cosmetic and therapeutic applications.

In a still further aspect, the present invention relates to a method for the cosmetic treatment of the skin, such as for treating wrinkles of the skin and facial asymmetries, the method comprising locally administering an effective amount of *botulinum* toxin to a patient by intradermal, subdermal or subcutaneous injection using the prefilled glass syringe according to the first aspect of the present invention.

This still further aspect is closely related to other aspects of the present invention described above and, thus, all comments, definitions and explanations given above in relation to these other aspects equally apply, unless otherwise stated.

The present invention will now be further illustrated by the following, non-limiting examples.

EXAMPLES

The following examples demonstrate the superior long-term stability of an aqueous *botulinum* toxin formulation in different prefilled syringe systems (in the following referred to as "configurations") according to the present invention.

The results obtained for the different syringe configurations surprisingly show that, contrary to expectation and common belief in the art, an aqueous *botulinum* toxin formulation stored in a prefilled syringe system is stable for a prolonged time period (e.g., up to 18 months) at standard refrigerator temperature (2-8° C.) and is even stable when stored for about 9 months at an elevated temperature of 25° C. Furthermore, extrapolation of the measured stability data indicates that the prefilled *botulinum* toxin syringe allows the provision of a shelf life at 2-8° C. of about 24 months and even longer.

Overall, the results obtained show that *botulinum* toxin can be conveniently used via prefilled syringes. This is an important contribution to the management of a wide variety of *botulinum* toxin-treated therapeutic and cosmetic indications since *botulinum* toxin prefilled syringes are safer and more convenient to use for clinicians and patients compared to conventional lyophilized *botulinum* toxin products, and offer flexibility and excellent shelf life.

Materials & Methods

The liquid *botulinum* toxin formulation used in the following examples was prepared by dissolving 1.0 mg human albumin, 4.7 mg sucrose and incobotulinumtoxinA in 0.9% saline to a concentration of 50 U/ml.

The *botulinum* toxin solution was then filled into a syringe glass barrel pre-assembled with a Luer-Lock-type closure comprising a Luer-Lock adaptor and a tip cap which, when fitted, contacts the opening of the distal syringe tip in order to seal the syringe barrel. A plunger stopper was inserted into the proximal end portion of the barrel in order to close the proximal opening. The resulting prefilled syringe was then stored at a temperature of about 5° C., 25° C., and 30° C.

The stability of the *botulinum* toxin solution was determined initially and after a storage time of one month, three months, six months and nine months by measuring the remaining toxin potency, the pH value, and the subvisible particles level.

The potency was determined using a hemidiaphragm assay. The assay is conducted using a murine nerve muscle preparation which is maintained in an organ bath containing 4 ml of medium. The muscle is attached to a force transducer and electrically stimulated via the phrenic nerve resulting in a isometric contraction force which remains constant for more than 180 min if no toxin is added. Upon introduction of toxin to the organ bath, the contraction amplitude of the nerve-stimulated muscle gradually declines. The contraction amplitude of the diaphragm is monitored over time. As a read-out, the time at which half the intial contraction force is reached is determined and referred to as paralysis time. The paralysis time is proportional to the amount of active toxin added to the preparation.

The pH measurements were performed in accordance with the US Pharmacopeia standardized test method USP <791>, which outlines pH measurements for a multitude of pharmaceutical product, using a pH meter (Lab 870, Schott Instruments).

Particle measurements were conducted using Micro-Flow Imaging. The Micro-Flow Imaging measurements were conducted using a DPA-5200 particle analyzer system (ProteinSimple, Santa Clara, Calif., USA) equipped with a silane coated high-resolution 100 µm flow cell. The samples were analyzed undiluted. MFI View System Software (MVSS) version 2-R2-6.1.20.1915 was used to perform the measurements, and MFI View Analysis Suite (MVAS) software version 1.3.0.1007 was used to analyze the samples.

Four different prefilled syringe systems (or "syringe configurations"), which differ from each other by the syringe barrel, tip cap and/or plunger stopper, were examined and are summarized in Table 1.

TABLE 1

Syringe configurations A, B, G, and H studied

| CONF. | COMP. | SYRINGE BARREL Product name | SYRINGE BARREL Material | TIP CAP Product name | TIP CAP Material | PLUNGER STOPPER Product Name | PLUNGER STOPPER Material |
|---|---|---|---|---|---|---|---|
| A | GH[1] | RTF® 1.0 ml long Luer Lock syringe with TELC[4] | Borosilicate glass of type 1; inner surface of glass barrel is siliconized by "Baked on Siliconization"[3]; sterilized by EtO | Helvoet® FM 27 Grey[1] | Styrene-butadiene rubber compound (free from MBT(2-mercaptobenzothiazole)) | West® 4023/50 Gray with FluroTec® coating | Bromobutyl elastomer reinforced with an inert mineral and coated with a FluroTec® film |
| B | GH[1] | RTF® 1.0 ml long Luer Lock syringe with TELC[4] | See Config. A | Helvoet® FM 27 grey[1] | See Config. A | West® 4023/50G NovaPure® | Elastomer formulation coated with FluroTec® barrier film |
| G | BD[2] | BD Hypak SCF™ 1 ml PRTC[6] | Borosilicate type I glass; inner surface of glass barrel is siliconized using a silicone oil; sterilized by EtO (ethylene oxide) | PRTC FM 27 Grey[5] | Styrene-butadiene rubber compound (free from MBT) | BD Hypak™ BSCF 4023/50 grey FluroTec® (West®)[7] | Bromobutyl elastomer reinforced with an inert mineral and coated with a FluroTec® film |
| H | BD[2] | BD Hypak SCF™ 1 ml PRTC[6] | See Config. G | PRTC 7025/65 grey (West®)[5] | Synthetic isoprene-bromobutyl blend reinforced with an inert mineral | BD Hypak™ BSCF 4023/50 grey FluroTec® (West®)[7] | See Config. G |

[1] = Gerresheimer
[2] = Becton, Dickinson and Company
[3] = Use of Dow Corning® 365, Dimethicone NF emulsion
[4] = TELC (tamper evident Luerock Closure)
[5] = PRTC (plastic rigid tip cap)
[6] = SCF (sterile, clean and ready-to-fill)
[7] = BSCF (bagged sterile, clean and ready-to fill; utilizes bagged (BSCF) stoppers)

Results

The results of the stability measurements for configurations A, B, G, and H are shown in Table 2 below.

TABLE 2

Stability in terms of potency

STABILITY
(toxin potency in %, relative to the initial toxin activity)

| CONFIG. | Temperature | t = 0 (initial)* | 1 | 3 | 6 | 9 | 12 | 18 |
|---|---|---|---|---|---|---|---|---|
| A | 2-8° C. | 100 | 102 | 102 | 100 | 107 | 109 | 88 |
| B |  | 100 | 109 | 96 | 102 | 102 | 96 | 109 |
| G |  | 100 | 100 | 100 | 96 | 91 | 102 | 96 |
| H |  | 100 | 100 | 114 | 102 | 112 | 100 | 108 |
| A | 25° C. | 100 | 98 | 102 | 107 | 93 | 89 | 73 |
| B |  | 100 | 102 | 100 | 107 | 94 | 107 | 87 |
| G |  | 100 | 93 | 104 | 96 | 98 | 98 | 75 |
| H |  | 100 | 108 | 116 | 100 | 90 | 80 | 73 |
| A | 30° C. | 100 | 84 | 91 | 80 | — | — | — |
| B |  | 100 | 106 | 93 | 87 | — | — | — |
| G |  | 100 | 88 | 93 | 84 | — | — | — |
| H |  | 100 | 92 | 114 | 94 | — | — | — |

*= The initial absolute toxin activity in units ranges from 51 U to 56 U.

Figure 1:
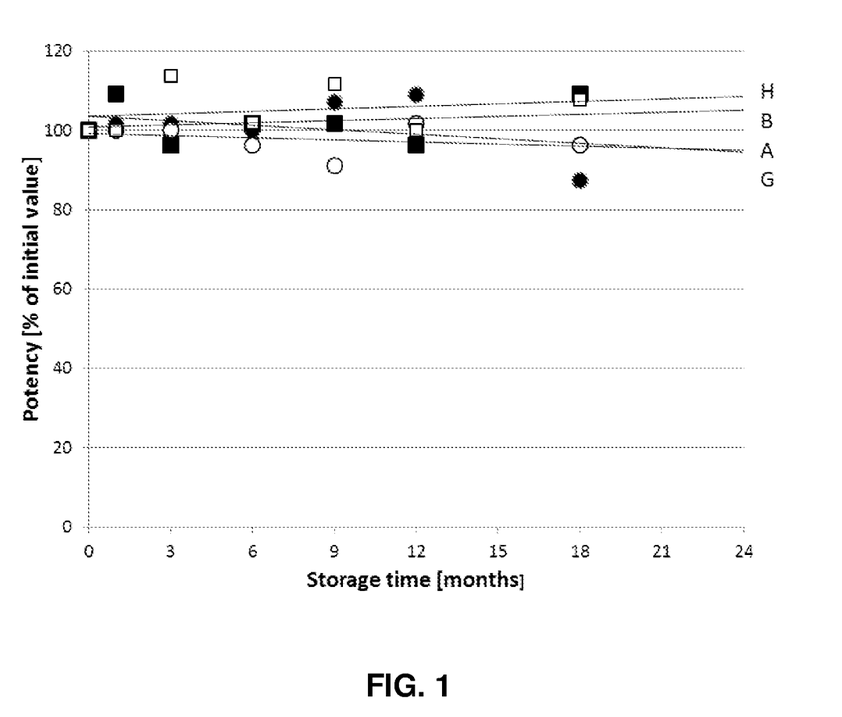
FIG. 1 shows the stability of a liquid *botulinum* toxin formulation in prefilled syringe configurations A, B, G, and H at 5° C. as a function of time. Configuration A: (●), configuration B (■), configuration H: (□), configuration G: (○).
Figure 2:
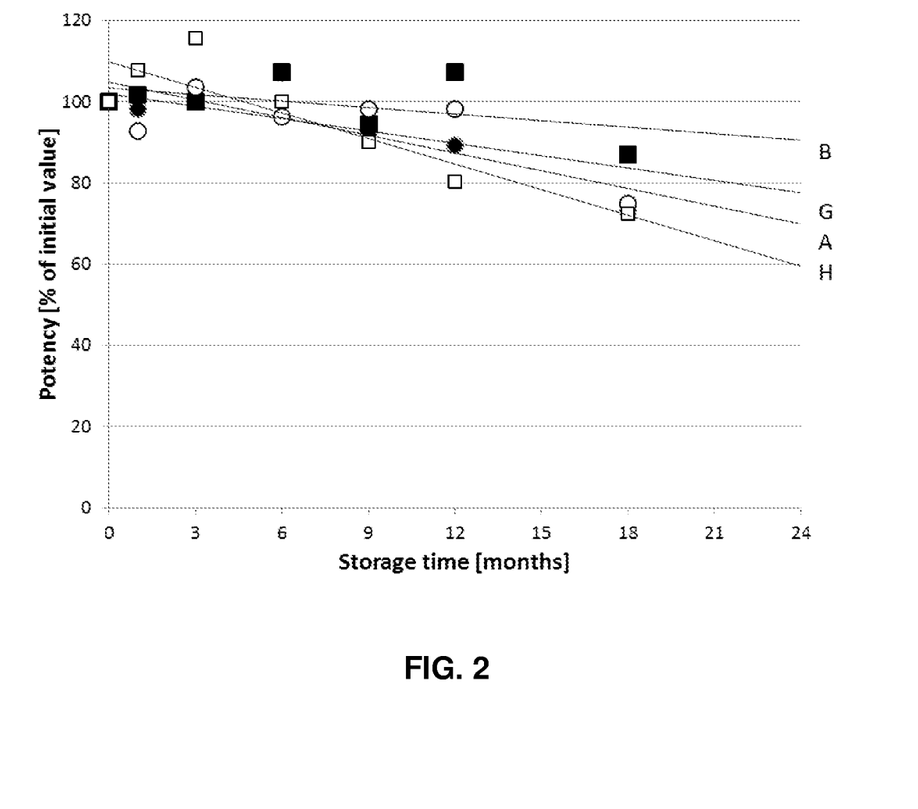
FIG. 2 shows the stability of a liquid *botulinum* toxin formulation in prefilled syringe configurations A, B, G, and H at 25° C. as a function of time. Configuration A: (●), configuration B (■), configuration H: (□), configuration G: (○).
Figure 3:
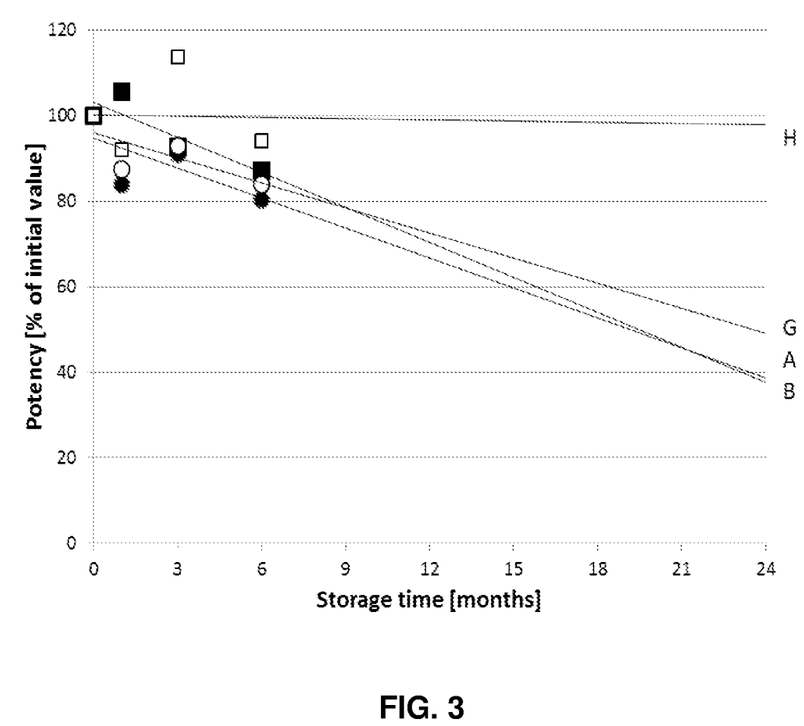
FIG. 3 shows the stability of a liquid *botulinum* toxin formulation in prefilled syringe configurations A, B, G, and H at 30° C. as a function of time. Configuration A: (●), configuration B (■), configuration H: (□), configuration G: (○).

The above stability data are, together with an extrapolation to a storage time of 24 months, graphically shown in FIG. 1 (stability at 2-8° C.), FIG. 2 (stability at 25° C.), and FIG. 3 (stability at 30° C.). As can be seen from Table 2 and FIGS. 1-3, the maximum measured loss of biological activity is only 12%, 20%, and 20% for the temperature conditions 2-8° C. (up to 18 months), 25° C. (up to 12 months), and 30° C. (up to 6 months), respectively. Extrapolations indicate that the loss in biological activity after a storage time of 24 months is less than 5% at 2-8° C. for all configurations A, B, G, and H, and less than 10% at 25° C. for configuration B.

Furthermore, the pH measurements revealed that the pH remained exceptionally stable over a period of up to 18 months. No trend towards higher or lower values was observed and all measured pH values remained within ±0.5 of the initial pH (see Table 3).

TABLE 3

Stability in terms of pH

STABILITY
(pH)

| CONFIG. | Temperature | t = 0 (initial) | 1 | 3 | 6 | 9 | 12 | 18 |
|---|---|---|---|---|---|---|---|---|
| A | 2-8° C. | 6.8 | 6.8 | 7.0 | 7.1 | 6.5 | n.d.* | 6.8 |
| B |  | 7.0 | 6.7 | 6.9 | 6.9 | 6.6 | n.d. | 6.7 |
| G |  | 6.8 | 6.7 | 6.7 | 6.8 | 6.6 | n.d. | 6.7 |
| H |  | 6.4 | 6.2 | 6.6 | 6.4 | 6.9 | 6.6 | n.d. |
| A | 25° C. | 6.8 | 6.8 | 7.0 | 7.0 | 6.6 | 6.9 | 6.5 |
| B |  | 7.0 | 6.7 | 6.9 | 7.0 | 6.7 | 7.0 | 6.7 |
| G |  | 6.8 | 6.7 | 6.7 | 6.8 | 6.7 | 6.8 | 7.0 |
| H |  | 6.4 | 6.3 | 6.8 | 6.6 | 6.7 | 6.6 | n.d. |
| A | 30° C. | 6.8 | 6.8 | 7.0 | 7.0 | — | — | — |
| B |  | 7.0 | 6.8 | 6.9 | 7.1 | — | — | — |
| G |  | 6.8 | 6.8 | 6.7 | 6.9 | — | — | — |
| H |  | 6.4 | 6.4 | 6.8 | 6.6 | — | — | — |

*n.d. = not determined

Moreover, the particle size measurements by Micro-Flow Imaging showed no significant increase in the particle count (see Table 4).

TABLE 4

Stability in terms of the subvisible particle count

STABILITY
(subvisible particle count (equal to or greater than 10 μm))

| CONFIG. | Temperature | t = 0 (initial) | 1 | 3 | 6 | 9 | 12 | 18 |
|---|---|---|---|---|---|---|---|---|
| A | 2-8° C. | 27 | 63 | 14 | 27 | 69 | 64 | 162 |
| B |  | 69 | 80 | 26 | 9 | 64 | 27 | 58 |
| G |  | 18 | 101 | 48 | 125 | 133 | 83 | 351 |
| H |  | 545 | 139 | 59 | 163 | 223 | n.d. | n.d. |
| A | 25° C. | 27 | 74 | 25 | 43 | 5 | 53 | 127 |
| B |  | 69 | 22 | 11 | 15 | 129 | 146 | 143 |
| G |  | 18 | 176 | 110 | 67 | 105 | 81 | 378 |
| H |  | 545 | 345 | 227 | 86 | 756 | 327 | n.d. |
| A | 30° C. | 27 | 27 | 15 | 53 | — | — | — |
| B |  | 69 | 42 | 30 | 89 | — | — | — |
| G |  | 18 | 78 | 89 | 90 | — | — | — |
| H |  | 545 | 475 | 150 | 396 | — | — | — |

As can be seen from Table 4, the particle counts stay well below 1000/ml and in most cases even below 200/ml. Likewise, particle measurements by means of the resonant mass measurement method (using the ARCHIMEDES particle methodology system; Affinity Biosensors, Santa Barbara, Calif., USA) and nanoparticle tracking analysis (using a NanoSight LM20 system; NanoSight, Amesbury, UK) revealed no relevant particle counts.

In conclusion, the results presented above show that liquid *botulinum* toxin formulations in prefilled syringes are stable for a prolonged period at temperatures of 2-8° C. and even at ambient temperatures (e.g., 25° C. to 30° C.). In view of the fact that *botulinum* toxins are inherently instable, in particular at low toxin concentrations, this finding was unexpected. In particular, *botulinum* toxins are known to be highly heat-labile and highly unstable at alkaline pH. Therefore, given the labile nature of *botulinum* toxins, the finding that *botulinum* toxin in aqueous solution is highly stable, when stored in prefilled syringes, was highly surprising.

The *botulinum* toxin prefilled syringe according to the present invention therefore offers significant advantages over other ways to deliver *botulinum* toxin, including enhancing convenience and ease of handling, reducing medication errors, improving dosing accuracy, minimizing the risk of contamination, improving sterility assurance, and increasing safety in administration.

The invention claimed is:

1. A prefilled glass syringe comprising an aqueous *botulinum* toxin formulation, the glass syringe comprising
   (a) a syringe barrel made of glass including a proximal end and a distal end, and a cylindrical wall extending therebetween and defining a barrel lumen, the syringe barrel having a distally projecting tip with a fluid passage extending therethrough and communicating with the barrel lumen, wherein the cylindrical wall has an interior surface optionally coated with a barrier layer,
   (b) a capping device having an outlet engaging portion sealingly engaging and closing the distal open outlet end of the syringe, wherein the outlet engaging portion is made of an elastomeric material that optionally has a coating on its surface, and
   (c) a plunger rod assembly which extends into the proximal end of the syringe barrel and includes a plunger stopper in sliding fluid-tight engagement with the cylindrical wall of the barrel lumen, wherein the plunger stopper is made of an elastomeric material, which optionally has a coating on at least a portion of the plunger stopper that contacts the aqueous *botulinum* toxin formulation during storage and/or injection,
   wherein the elastomeric material of the outlet engaging portion is selected from the group consisting of isoprene rubber, butadiene rubber, butyl rubber, halogenated butyl rubber, styrene-butadiene rubber, and mixtures thereof, and
   the elastomeric material of the plunger stopper is selected from the group consisting of isoprene rubber, butadiene rubber, butyl rubber, halogenated butyl rubbers, styrene-butadiene rubber, and mixtures thereof, and
   wherein the toxin activity is not reduced by more than 25%, relative to the initial toxin activity, upon storage of the prefilled glass syringe for 12 months at 5° C. or 12 months at 25° C.

2. The prefilled glass syringe of claim 1, wherein the number of subvisible particles of equal to or greater than 10 μm is below 1000/ml during storage for 6 to 24 months at 2° C. to 30° C.

3. The prefilled glass syringe of claim 1, wherein the pH value is not increased or decreased by more than 10%, relative to the initial pH value, upon storage of the prefilled glass syringe for 6 to 12 months at 5° C. or 25° C., or wherein the pH of the aqueous *botulinum* toxin formulation during storage is maintained in the range of 6.0 to 7.5, or both.

4. The prefilled glass syringe of claim 1, wherein the *botulinum* toxin is present in the aqueous formulation at a concentration of 10 U/ml to 1000 U/ml.

5. The prefilled glass syringe of claim 1, wherein the aqueous *botulinum* toxin formulation in the prefilled glass syringe does not contain a buffer.

6. The prefilled glass syringe of claim 1, wherein the optional coating on the outlet engaging portion is present and is a crosslinked silicone coating or a fluoropolymer coating.

7. The prefilled glass syringe of claim 1, wherein the barrier layer of the syringe barrel is present and is a silicone-free layer or a silicone layer.

8. A kit comprising a prefilled glass syringe according to claim 1 and, optionally, instructions for use of said prefilled glass syringe.

9. A method of treating a disease or condition caused by or associated with hyperactive cholinergic innervation of muscles or exocrine glands in a patient, the method comprising locally administering an effective amount of *botulinum* toxin to a muscle or exocrine gland of the patient by injection using the prefilled glass syringe according to claim 1.

10. A method for the cosmetic treatment of the skin, optionally for treating wrinkles of the skin and facial asymmetries, the method comprising locally administering an effective amount of *botulinum* toxin to a patient by intradermal, subdermal or subcutaneous injection using the prefilled glass syringe according to claim 1.

11. The prefilled glass syringe of claim 1, wherein the optional coating on the plunger stopper is present and is a crosslinked silicone coating or a fluoropolymer coating.

12. The method of claim 9, wherein the disease or condition caused by or associated with hyperactive cholinergic innervation of muscles or exocrine glands is selected from dystonia, spasticity, paratonia, diskinesia, focal spasm, strabismus, tremor, tics, migraine, sialorrhea and hyperhidrosis.

13. The prefilled glass syringe of claim 1, wherein the toxin activity is not reduced by more than 25%, relative to the initial toxin activity, upon storage of the prefilled glass syringe for 12 months at 5° C.

14. The prefilled glass syringe of claim 1, wherein the toxin activity is not reduced by more than 25%, relative to the initial toxin activity, upon storage of the prefilled glass syringe for 12 months at 25° C.

15. A kit according to claim 8, comprising instructions for use of said prefilled glass syringe.

16. A method according to claim 10, comprising treating wrinkles of the skin and facial asymmetries.

* * * * *